United States Patent
Michaud et al.

(10) Patent No.: US 10,357,603 B2
(45) Date of Patent: Jul. 23, 2019

(54) ELECTROMAGNETIC SIGNAL-BASED INFUSION PUMP CONTROL

(71) Applicant: Tandem Diabetes Care, Inc., San Diego, CA (US)

(72) Inventors: Michael Michaud, San Diego, CA (US); Justin Brown, San Diego, CA (US); Caleb Butler, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 15/868,461

(22) Filed: Jan. 11, 2018

(65) Prior Publication Data
US 2018/0193555 A1    Jul. 12, 2018

Related U.S. Application Data

(60) Provisional application No. 62/445,041, filed on Jan. 11, 2017.

(51) Int. Cl.
*A61M 5/00* (2006.01)
*A61M 5/142* (2006.01)
*A61M 5/172* (2006.01)

(52) U.S. Cl.
CPC ...... *A61M 5/14248* (2013.01); *A61M 5/1723* (2013.01); *A61M 2205/3569* (2013.01); *A61M 2205/3584* (2013.01); *A61M 2205/50* (2013.01); *A61M 2205/502* (2013.01); *A61M 2205/505* (2013.01); *A61M 2205/587* (2013.01); *A61M 2205/8206* (2013.01);
(Continued)

(58) Field of Classification Search
CPC .. A61M 2205/3569; A61M 2205/8237; A61M 2205/8243
See application file for complete search history.

(56) References Cited

U.S. PATENT DOCUMENTS

| 5,582,593 A | 12/1996 | Hultman |
| 5,860,957 A | 1/1999 | Jacobsen et al. |

(Continued)

FOREIGN PATENT DOCUMENTS

| WO | WO 2009/013736 A2 | 1/2009 |
| WO | WO 2009/016636 A2 | 2/2009 |

OTHER PUBLICATIONS

Wu et al., Wireless Power and Data Transfer via a Common Inductive Link Using Frequency Division Multiplexing, Jul. 9, 2015, IEEE Transactions on Industrial Electronics, vol. 62, Iss. 12, p. 1-10.*

(Continued)

*Primary Examiner* — William R Carpenter
(74) *Attorney, Agent, or Firm* — Patterson Thuente Pedersen, P.A.

(57) ABSTRACT

A user-wearable infusion pump system includes an inductively or otherwise wirelessly chargeable battery and at least one button. Activation of the at least one button when not in the presence of an inductive charging signal can enable and/or initiate a first function or operation and activation of the at least one button in the presence of an inductive charging signal can enable and/or initiate a different, second function or operation. Such functionality can also be enabled in the presence of other types of electromagnetic signals.

22 Claims, 6 Drawing Sheets

(52) U.S. Cl.
CPC .............. *A61M 2205/8237* (2013.01); *A61M 2205/8243* (2013.01); *A61M 2209/01* (2013.01); *A61M 2230/201* (2013.01)

(56) References Cited

U.S. PATENT DOCUMENTS

| | | | |
|---|---|---|---|
| 6,070,761 A | 6/2000 | Bloom et al. | |
| 6,165,155 A | 12/2000 | Jacobsen et al. | |
| 6,402,689 B1 | 6/2002 | Scarantino et al. | |
| 6,514,689 B2 | 2/2003 | Han et al. | |
| 6,561,978 B1 | 5/2003 | Conn et al. | |
| 6,649,403 B1 | 11/2003 | McDevitt et al. | |
| 6,656,159 B2 | 12/2003 | Flaherty | |
| 6,960,192 B1 | 11/2005 | Flaherty et al. | |
| 6,963,770 B2 | 11/2005 | Scarantino et al. | |
| 6,970,742 B2 | 11/2005 | Mann et al. | |
| 7,010,340 B2 | 3/2006 | Scarantino et al. | |
| 7,011,630 B2 | 3/2006 | Desai et al. | |
| 7,144,384 B2 | 12/2006 | Gorman et al. | |
| 7,181,505 B2 | 2/2007 | Haller et al. | |
| 7,193,521 B2 | 3/2007 | Moberg et al. | |
| 7,198,603 B2 | 4/2007 | Penner et al. | |
| 7,303,549 B2 | 12/2007 | Flaherty et al. | |
| 7,316,899 B2 | 1/2008 | McDevitt et al. | |
| 7,366,925 B2 | 4/2008 | Keely et al. | |
| 7,385,443 B1 | 6/2008 | Denison | |
| 7,399,401 B2 | 7/2008 | Rush | |
| 7,483,743 B2 | 1/2009 | Mann et al. | |
| 7,497,827 B2 | 3/2009 | Brister et al. | |
| 7,558,629 B2 | 7/2009 | Keime et al. | |
| 7,604,593 B2 | 10/2009 | Parris et al. | |
| 7,605,710 B2 | 10/2009 | Crnkovich et al. | |
| 7,651,868 B2 | 1/2010 | McDevitt et al. | |
| 7,699,775 B2 | 4/2010 | Desai et al. | |
| 7,704,227 B2 | 4/2010 | Moberg et al. | |
| 7,711,402 B2 | 5/2010 | Shults et al. | |
| 7,713,574 B2 | 5/2010 | Brister et al. | |
| 7,714,757 B2 | 5/2010 | Denison et al. | |
| 7,737,581 B2 | 6/2010 | Spurlin et al. | |
| 7,774,145 B2 | 8/2010 | Brauker et al. | |
| 7,775,975 B2 | 8/2010 | Brister et al. | |
| 7,811,279 B2 | 10/2010 | John | |
| 7,933,780 B2 | 4/2011 | De La Huerga | |
| 7,949,382 B2 | 5/2011 | Jina | |
| 7,973,667 B2 | 7/2011 | Crnkovich et al. | |
| 8,005,547 B2 | 8/2011 | Forsberg et al. | |
| 8,034,019 B2 | 10/2011 | Nair et al. | |
| 8,100,852 B2 | 1/2012 | Moberg et al. | |
| 8,106,534 B2 | 1/2012 | Spurlin et al. | |
| 8,234,128 B2 | 7/2012 | Martucci et al. | |
| 8,280,476 B2 | 10/2012 | Jina | |
| 8,287,495 B2 | 10/2012 | Michaud et al. | |
| 8,311,749 B2 | 11/2012 | Brauker et al. | |
| 8,323,188 B2 | 12/2012 | Tran | |
| 8,369,919 B2 | 2/2013 | Kamath et al. | |
| 8,414,523 B2 | 4/2013 | Blomquist et al. | |
| 8,444,595 B2 | 5/2013 | Brukalo et al. | |
| 8,449,523 B2 | 5/2013 | Brukalo et al. | |
| 8,454,557 B1 | 6/2013 | Qi et al. | |
| 8,573,027 B2 | 11/2013 | Rosinko et al. | |
| 8,639,288 B1* | 1/2014 | Friedman ................ | A61M 5/20 455/556.1 |
| 8,986,253 B2 | 3/2015 | DiPerna | |
| 9,049,982 B2 | 6/2015 | Brukalo | |
| 9,155,900 B2 | 10/2015 | Meskens | |
| 9,381,297 B2 | 7/2016 | Brown et al. | |
| 9,750,873 B2 | 9/2017 | Brown et al. | |
| 2004/0010207 A1 | 1/2004 | Flaherty et al. | |
| 2005/0060030 A1 | 3/2005 | Lashinski et al. | |
| 2006/0173444 A1 | 8/2006 | Choy et al. | |
| 2007/0150019 A1 | 6/2007 | Youker et al. | |
| 2008/0097912 A1 | 4/2008 | Dicks et al. | |
| 2008/0097913 A1 | 4/2008 | Dicks et al. | |
| 2008/0097914 A1 | 4/2008 | Dicks et al. | |
| 2008/0097917 A1 | 4/2008 | Dicks et al. | |
| 2008/0125700 A1 | 5/2008 | Moberg et al. | |
| 2008/0208627 A1* | 8/2008 | Skyggebjerg ..... | A61M 5/14248 705/2 |
| 2008/0215035 A1 | 9/2008 | Yodfat et al. | |
| 2008/0215120 A1 | 9/2008 | Dicks et al. | |
| 2008/0224852 A1 | 9/2008 | Dicks et al. | |
| 2008/0231226 A1 | 9/2008 | Hoffman et al. | |
| 2009/0069868 A1* | 3/2009 | Bengtsson ........ | A61M 5/14248 607/60 |
| 2009/0115628 A1 | 5/2009 | Dicks et al. | |
| 2009/0177142 A1 | 7/2009 | Blomquist et al. | |
| 2009/0192366 A1 | 7/2009 | Mensinger et al. | |
| 2009/0192724 A1 | 7/2009 | Brauker et al. | |
| 2009/0192745 A1 | 7/2009 | Kamath et al. | |
| 2009/0209945 A1 | 8/2009 | Lobl et al. | |
| 2009/0240193 A1 | 9/2009 | Mensinger et al. | |
| 2009/0254037 A1* | 10/2009 | Bryant, Jr. ............ | A61M 5/142 604/151 |
| 2010/0093319 A1* | 4/2010 | Sherman ........... | H04M 3/42178 455/414.1 |
| 2010/0121169 A1 | 5/2010 | Petisce et al. | |
| 2010/0134305 A1 | 6/2010 | Lu et al. | |
| 2010/0179402 A1 | 7/2010 | Goode, Jr. et al. | |
| 2010/0198142 A1 | 8/2010 | Sloan et al. | |
| 2010/0234709 A1 | 9/2010 | Say et al. | |
| 2010/0324382 A1 | 12/2010 | Cantwell et al. | |
| 2011/0040251 A1 | 2/2011 | Blomquist et al. | |
| 2011/0066555 A1 | 3/2011 | Dicks et al. | |
| 2011/0078441 A1 | 3/2011 | Dicks et al. | |
| 2011/0172744 A1 | 7/2011 | Davis et al. | |
| 2011/0190614 A1 | 8/2011 | Brister et al. | |
| 2011/0213329 A1 | 9/2011 | Yodfat et al. | |
| 2011/0213621 A1 | 9/2011 | Dicks et al. | |
| 2011/0257895 A1 | 10/2011 | Brauker et al. | |
| 2012/0029433 A1* | 2/2012 | Michaud ............. | A61M 5/1413 604/151 |
| 2012/0091813 A1 | 4/2012 | Spurlin et al. | |
| 2012/0095393 A1* | 4/2012 | Reinke ................... | G16H 40/63 604/66 |
| 2012/0185267 A1 | 7/2012 | Kamen et al. | |
| 2012/0232520 A1 | 9/2012 | Sloan et al. | |
| 2013/0053816 A1 | 2/2013 | DiPerna et al. | |
| 2013/0324928 A1 | 12/2013 | Kruse | |
| 2013/0331790 A1 | 12/2013 | Brown et al. | |
| 2014/0175682 A1* | 6/2014 | Johnson ................. | A61L 9/127 261/30 |
| 2014/0276423 A1 | 9/2014 | Lecanu-Fayet | |
| 2016/0339172 A1 | 11/2016 | Michaud et al. | |
| 2017/0049957 A1 | 2/2017 | Michaud | |
| 2017/0142658 A1 | 5/2017 | Kruse | |
| 2017/0173261 A1* | 6/2017 | O'Connor ............... | G06F 19/00 |
| 2018/0071454 A1 | 3/2018 | Betts et al. | |

OTHER PUBLICATIONS

Search Report and Written Opinion for PCT Application No. PCT/US2018/013331 dated May 3, 2018, 14 pages.

* cited by examiner

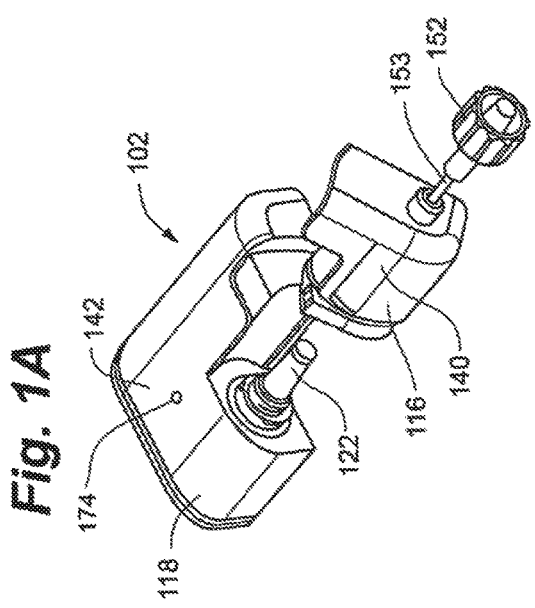
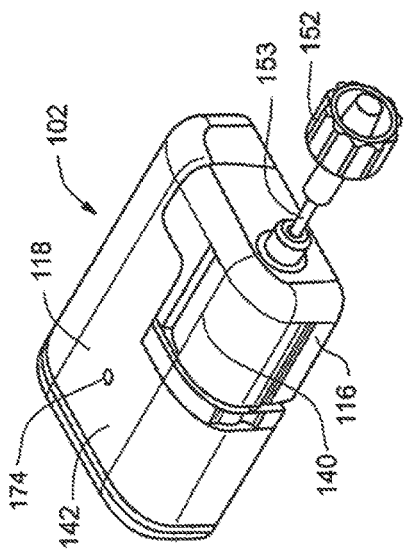
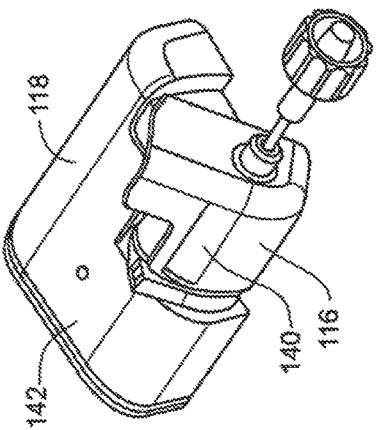

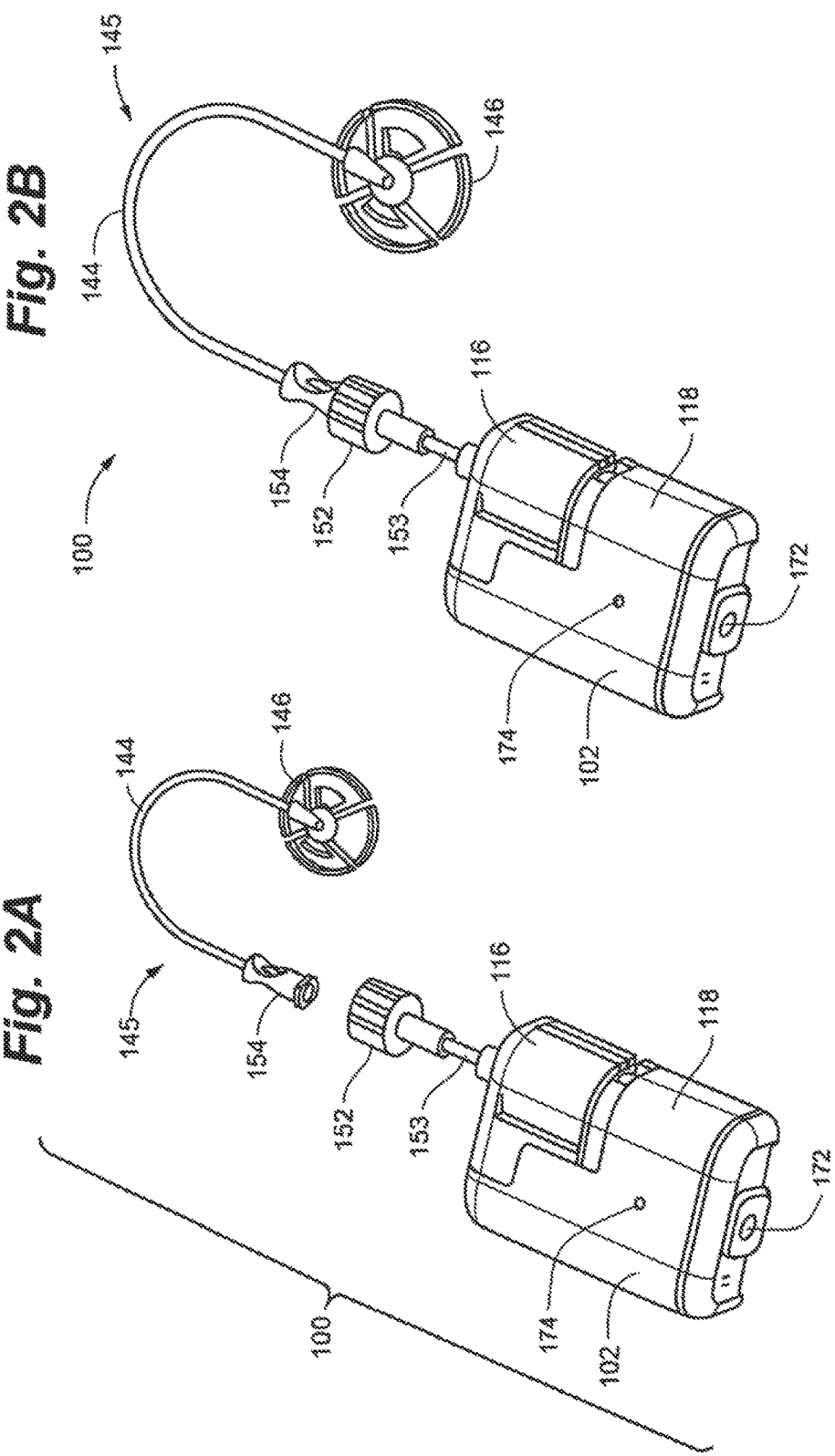

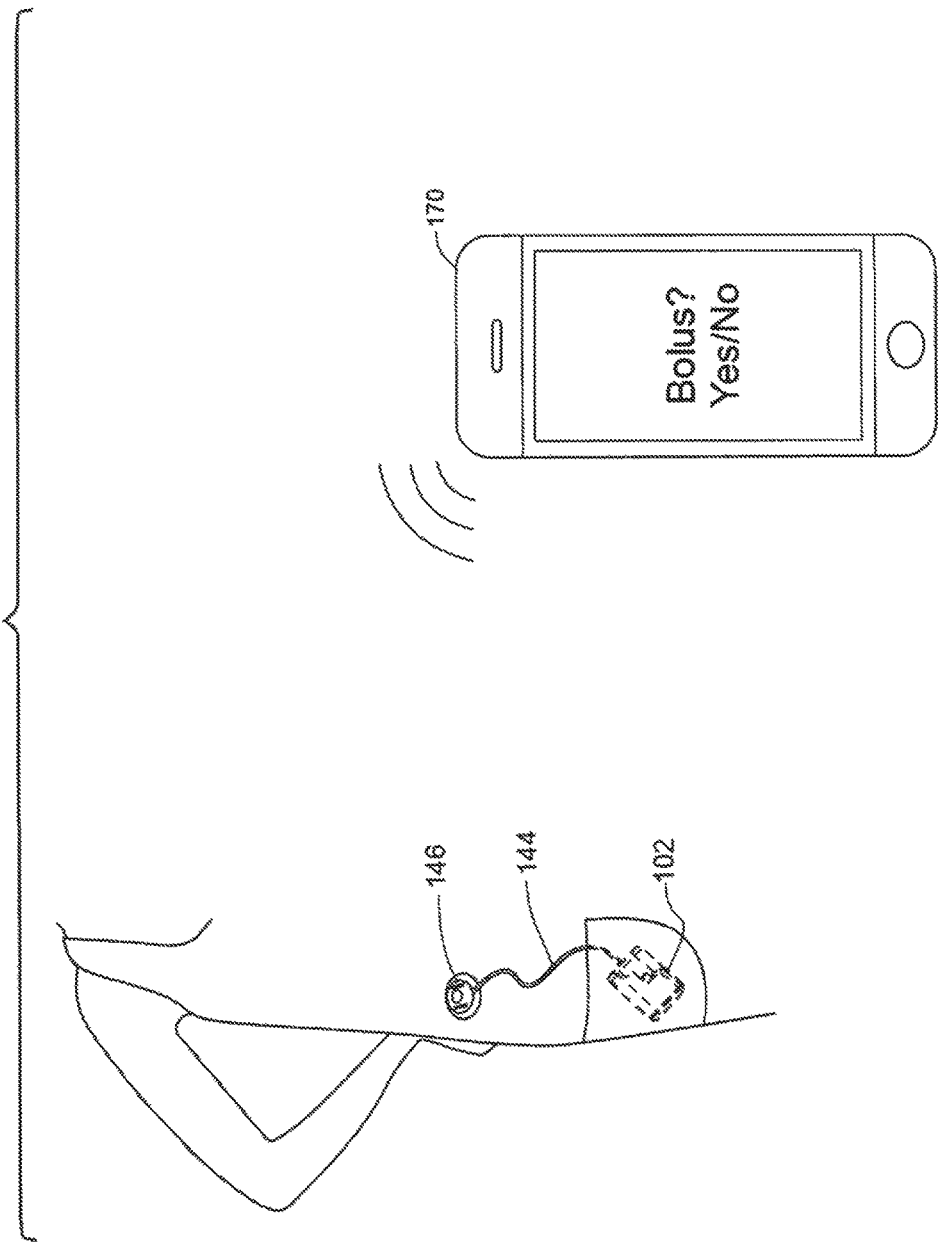

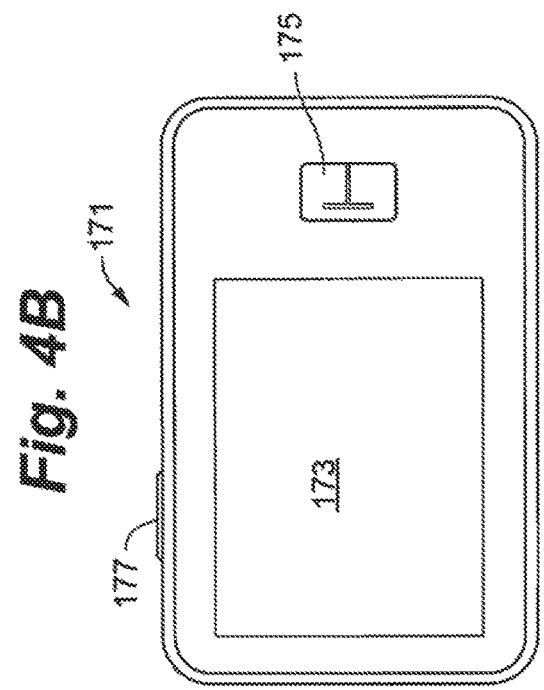
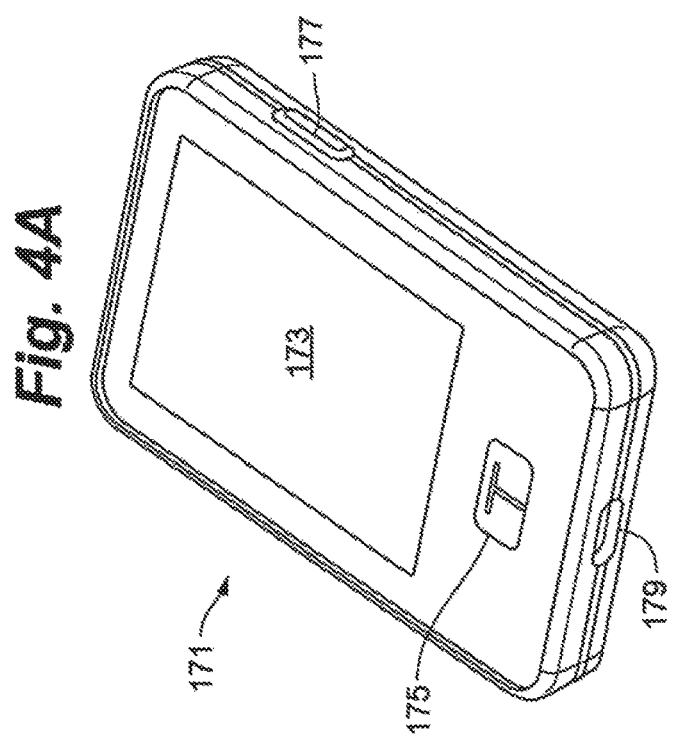

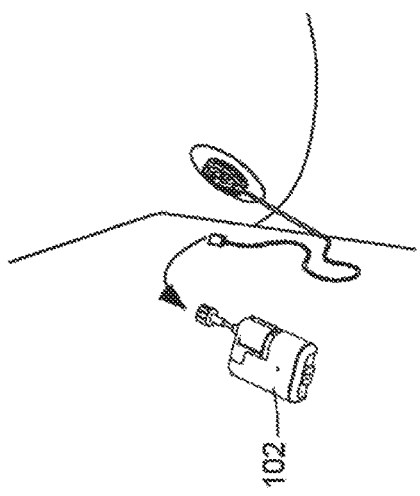
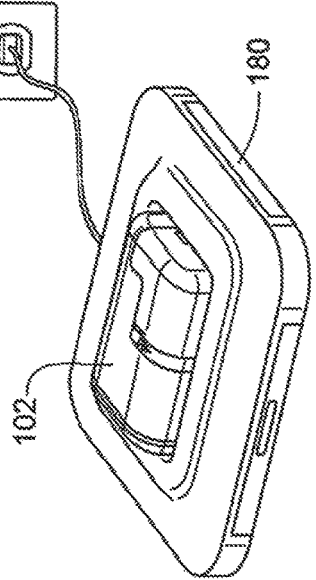
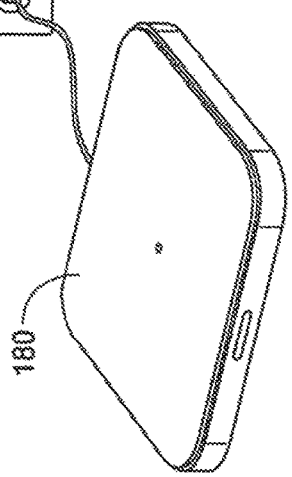
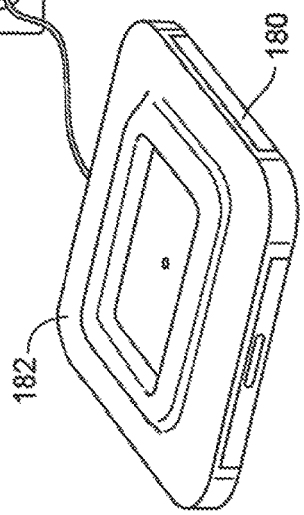

ELECTROMAGNETIC SIGNAL-BASED INFUSION PUMP CONTROL

RELATED APPLICATION

The present application claims the benefit of U.S. Provisional Application No. 62/445,041 filed Jan. 11, 2017, which is hereby incorporated herein in its entirety by reference.

TECHNICAL FIELD

The present invention relates to medical pumps for delivering medicament to a patient, and more specifically, to a user-wearable pump.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. Patent Application Publication No. 2013/0053816; U.S. Pat. Nos. 8,573,027; 8,986,253; U.S. Patent Application Publication No. 2013/0324928; U.S. Patent Application Publication No. 2013/0331790; U.S. Pat. No. 8,287,495; U.S. patent application Ser. No. 15/241,257 (filed Aug. 19, 2016); and U.S. patent application Ser. No. 15/158,125 (filed May 18, 2016), each of which is hereby incorporated herein by reference in its entirety.

One type of pump that has been developed is a patch pump, or micro pump. Patch pumps are small pumps, typically ambulatory, that may be carried directly on the skin under the user's clothing. In some cases, the pumps are situated directly on, or very near to, the injection site such that little or no tubing is required to deliver the insulin or other medicament to the patient. Some patch pumps include a single button on the pump to initiate delivery of medicament and do not include a built-in display or user interface. These pumps are therefore primarily remote-controlled. Having only a single button on the pump provides the advantage of being more robust for waterproofing and resistance to external contaminants. However, a disadvantage is that the functionality of a pump with a single button is limited without the use of a remote control apparatus, typically including a user interface.

SUMMARY

Embodiments of the present disclosure enable enhanced or altered functionality of an infusion pump in the presence of a recognized electromagnetic signal or following a predefined sequence of accelerometer-detected orientation shifts. For example, activation of at least one button on the pump normally initiates a first function or operation, such as initiating delivery of medicament, but in the presence of a recognized electromagnetic signal or following a predefined sequence of accelerometer-detected orientation shifts, the at least one button can initiate a second function or operation different from the first function, such as pairing the pump to a remote device. This can expand the number of functions that can be accomplished with a device that has a limited number of means for inputting commands into the device.

One embodiment of the present disclosure provides an infusion pump system including a pump for delivering medicament to a user of the pump. The pump can have a wirelessly chargeable battery and at least one button. When not in the presence of a wireless charging signal, activation of the at least one button can enable and/or initiate a first function or operation. When in the presence of a wireless charging signal, activation of the at least one button can enable and/or initiate a second, different function or operation.

Another embodiment of the present disclosure provides an infusion pump system including a pump for delivering medicament to a user of the pump. The pump can include a Bluetooth beacon receiver and at least one button. When not in the presence of a Bluetooth beacon, activation of the at least one button can enable and/or initiate a first function or operation. When in the presence of a Bluetooth beacon, activation of the at least one button can enable and/or initiate a second, different function or operation.

Another embodiment of the present disclosure provides an infusion pump system including a pump having for delivering medicament to a user of the pump. The pump can include a plurality of accelerometers that are configured to sense acceleration and detect pump orientation and at least one button. Activation of the at least one button can enable and/or initiate a first function or operation, but following a predefined sequence of accelerometer-detected orientation shifts, activation of the at least one button can enable and/or initiate a second, different function or operation.

In one embodiment, activation of the at least one button can be at least one of a single press of the at least one button or a predefined sequential pattern of presses of the at least one button over a determined length of time. In one embodiment, the first function can be at least one of initiating delivery of medicament, communicatively coupling the pump to a remote display and/or user interface, communicatively coupling the pump to a remote glucose monitor, or initiating a status check. In one embodiment, the second function can be at least one of suspending delivery of medicament, initiating a low-power mode for the pump, resetting the pump, communicatively coupling the pump to a remote display and/or user interface, communicatively coupling the pump to a remote glucose monitor, or initiating a test routine.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 1A-1C depicts an embodiment of a pump system according to the disclosure.

FIGS. 2A-2B depict an embodiment of a pump system according to the disclosure.

FIG. 3 depicts an embodiment of a pump system according to the disclosure.

FIGS. 4A-4B depict remote control devices for a pump system according to embodiments of the disclosure.

FIGS. 5A-5D depict a procedure for inductively charging a battery of a pump system according to an embodiment of the disclosure.

Figure 6:
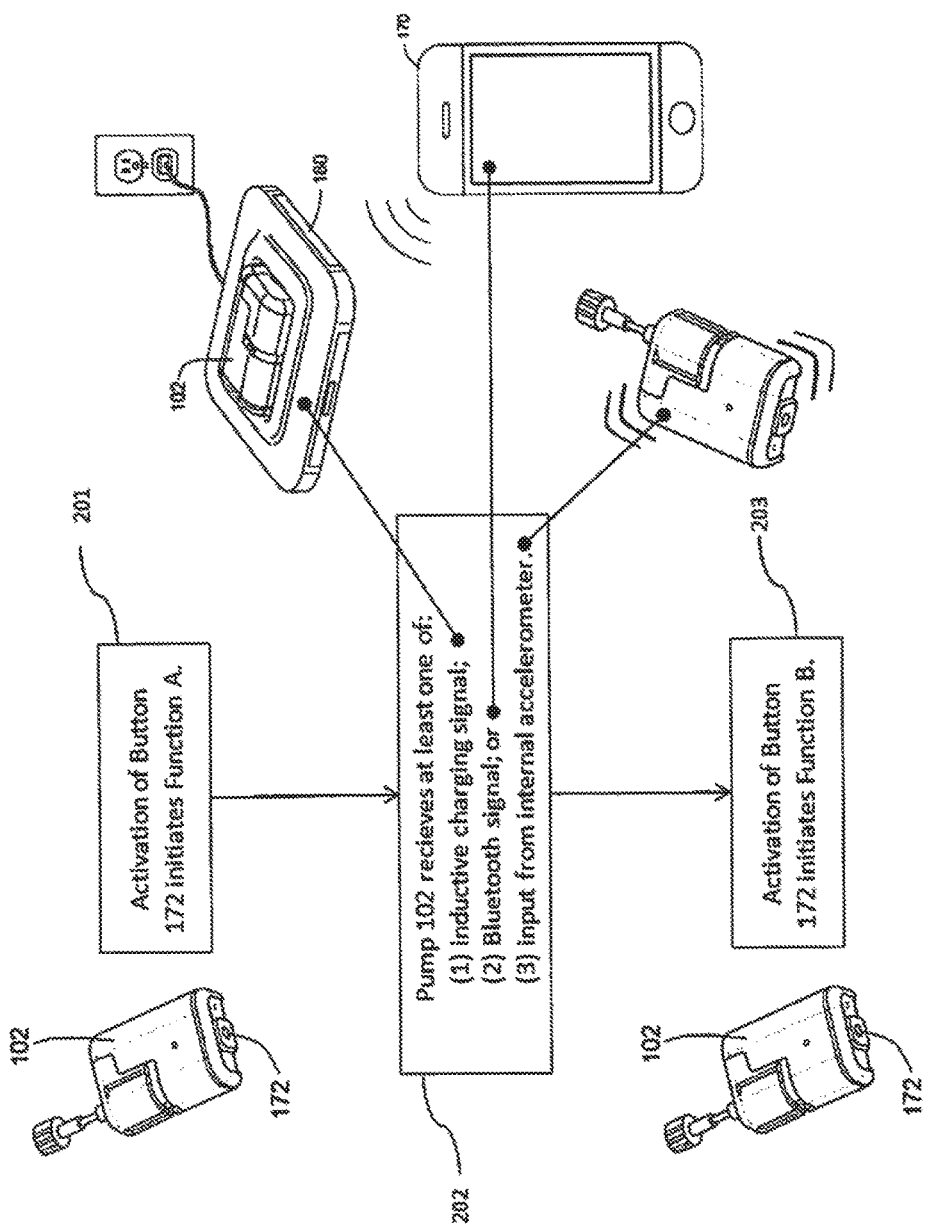
FIG. 6 depicts a method of altering or enhancing the functionality of a pump system according to embodiments of the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring to FIGS. 1A-1C, a pump system 100 including a pump 102 is depicted in accordance with an embodiment of the disclosure. Drive unit 118 of pump 102 includes a drive mechanism 122 that mates with a recess in medicament cartridge 116 of pump 102 to attach the medicament cartridge 116 to the drive unit 118. The drive unit 118 cooperates with the medicament cartridge to provide a delivery mechanism for delivery of medicament, such as insulin, from a reservoir in the medicament cartridge 116 to a user through, e.g., a cannula. Further details regarding example embodiments of such delivery mechanisms can be found in U.S. Patent Publication No. 2017/0049957, which is hereby incorporated by reference in its entirety.

Cartridge 116 of pump 102 can attach to drive unit 118 with, for example, a quarter turn attachment mechanism. The recess of cartridge 116 can be configured to initially attach to drive mechanism 122 of drive unit 118 such that an outer front housing surface 140 of the cartridge 116 is offset from an outer front housing surface 142 of the drive unit 118 and an angle of, e.g., between about 30 and about 150 degrees. The cartridge 116 can then be rotated toward the drive unit 118 to align the outer surface 140 of the cartridge 116 generally parallel with the outer surface 142 of the drive unit 118 and secure the cartridge 116 on the drive unit 118. In one embodiment, the engagement of the cartridge 116 to the drive unit 118 made by this rotation can cause an audible clicking sound that provides an auditory indication to the user that the cartridge is properly attached by the user of, e.g., detent projections and grooves as depicted. Such a feature can alternatively or additionally provide a tactile indication to the user that the cartridge is properly attached. Further details regarding such pumps can be found in U.S. patent application Ser. No. 14/707,851 (filed May 8, 2015); U.S. Patent Application Publication No. 2016/0339172; and U.S. Patent Application Publication No. 2017/0049957, each of which is hereby incorporated herein by reference in its entirety.

In one embodiment, pump system 100 can include a short length of tubing 153 and a connector 152. Connector 152 can be configured to attach to a corresponding connector of an infusion set that includes, e.g., a length of tubing extending from the corresponding connector to an infusion site having an infusion site connector to deliver medicament to the infusion site. In some embodiments, connector 152 extending from cartridge 116 and the corresponding connector of the infusion set can be Luer Lock connections. Other infusion set configurations and attachments are described in U.S. Patent Publication No. 2014/0276423, which is hereby incorporated by reference in its entirety.

As depicted in the embodiment of FIGS. 2A-2B, pump system 100 can include a pump 102 and an infusion set 145. FIG. 2A depicts this infusion set 145 as not connected to pump while FIG. 2B depicts infusion set 145 connected to pump 102 via connectors 154 and 152. Infusion set 145 can include tubing 144 extending between a connector 154 and a site connector 146. Connector 154 can be configured to couple to pump 102 at connector 152. Site connector 146 can be configured to be attached to an infusion site on a user, while pump 102 can be carried in a separate location, such as the user's pocket (as depicted in FIG. 3). Various lengths of tubing 144 can be used in this embodiment to accommodate the user's preference.

In one embodiment, pump 102 includes a processor that controls operations of the pump and, in some embodiments, may communicate in either one-way or two-way modes to, e.g., receive operational commands and/or other signals, including data, from a separate device and/or, e.g., to send signals, including data, to a separate device. Pump 102 can include one or more buttons configured to cause the processor to initiate one or more functions. In the depicted embodiments, pump 102 includes only a single button 172, although more than one button may be present on pump 102. Button 172 can be configured to, for example, initiate delivery of medicament. Any single button such as button 172 can be utilized to execute a plurality of functions or operations. For example, a single press of button may initiate one function, holding the button down for a predetermined period of time may initiate another function, etc. Because the depicted pump 102 optionally does not itself include a display or user interface, information and feedback regarding medicament delivery or dosing initiated with button 172 can be communicated to and displayed on a remote control device or other device having a display and/or other type of user interface.

In one embodiment, pump 102 includes a light source, such as a light emitting diode (LED) 174. Light source 174 can be configured to provide user feedback regarding user input and/or the performance of a desired function. For example, in one embodiment, light source 174 can illuminate or blink one or more times to indicate that the one or more buttons 172 have been activated and/or that a desired function has been initiated. In one embodiment, pump 102 can additionally and/or alternatively vibrate and/or provide audible notifications to indicate that the one or more buttons 172 have been activated and/or that a desired function has been initiated or, e.g., to provide user feedback regarding user input and/or the performance of the desired function. Illumination of light source 174 and/or vibrations and/or audible notifications may be executed in any number of patterns, frequencies, durations, sequences, combinations, colors, brightness levels, etc. to indicate particular information, such as particular input received and/or particular functions or operations enabled and/or initiated, to the pump user or caregiver.

Referring to FIGS. 3-4B, one or more remote control devices 170, 171 can be used to communicate with the processor of pump 102 to control delivery of medicament and transfer data with pump 102 via a wired or a wireless electromagnetic signal, such as via, e.g., a near field communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device 170, such as a smart phone (as depicted in FIG. 3) executing a software application for control of the pump, a dedicated remote controller 171 (as depicted in FIGS. 4A-4B), a wearable electronic watch or electronic health or fitness monitor or personal digital assistant (PDA), etc., or a tablet, laptop or personal computer. Such communications between (and among) the one or more remote control devices 170, 171 and pump 102 may be one-way or two-way for, e.g., effective transfer of data among the devices and the pump, control of pump operations, updating software on the devices and/or pump, and allowing pump-related data to be viewed on the devices and/or pump.

Referring to FIGS. 4A-4B for instance, a dedicated remote controller 171 according to embodiments of the disclosure can include a display or user interface such as a touchscreen display 173. Touchscreen 173 can, in various embodiments, include a color display and can be a capacitive touchscreen, resistive touchscreen, or the like and can be a single touch or multitouch touchscreen. Dedicated remote controller 171 can further include one or more touch sensitive buttons 175, a pushbutton 177 and a port 179. In some embodiments, touch sensitive button 175 can be configured to return the controller 171 to a home screen from another menu screen any time the button 175 is touched and the pushbutton 177 can be configured to wake the device from a sleep or off mode and activate the display 173 anytime the button 177 is pressed. In other embodiments, these functions can be reversed or both functions can be accomplished with a single button depending on the current state of the device. Port 179 can be any type of port known in the art for data transfer and charging of a rechargeable battery in the controller 171, such as, for example, a hardware interface such as a USB port, Thunderbolt® port, etc. Controller 171 can additionally include one or more of a speaker/microphone, vibrator and/or light, such as an LED, for providing alerts, alarms, notifications, voice inputs/commands, etc., single or in various combinations as previously described.

In some embodiments, pumps described herein can interface with a glucose meter, such as a blood glucose meter (BGM) or a continuous glucose monitor (CGM), the latter category of which provides a substantially continuous estimated of a blood glucose level through a transcutaneous sensor that measures analytes, such as glucose, in the patient's interstitial fluid rather than the patient's blood. Pump system can use data obtained from a glucose meter such as a CGM to adjust therapy with pump either automatically, such as in a closed-loop or semi-closed loop "artificial pancreas" system, or by providing such data for user review via a remote control device 170, 171. The data may be transmitted from the CGM to the pump and/or remote controller via a wireless transmitter, such as an NFC RF transmitter or an RF transmitter operating according to a "Wi-Fi" or Bluetooth® protocol or the like, or the data may be transmitted via a wire connector. Further detail regarding CGM systems and definitions of related terms can be found in, e.g., U.S. Pat. Nos. 8,311,749, 7,711,402 and 7,497,827, each of which is hereby incorporated by reference in its entirety.

Embodiments of the present invention include components capable of and methods using wired and wireless transmission and receipt of signals for exchange of information and commands between and among any of the components as described herein, including, e.g., between a pump and a smartphone; among a pump, a CGM and a smartphone; between a dedicated remote controller and a pump; among a dedicated remote controller, a CGM and a pump; among a dedicated remote controller, a BGM and a pump, and other combinations as would be contemplated by those of skill in the art.

Referring to FIGS. 5A-5C, pumps according to embodiments of the present disclosure can include one or more rechargeable batteries in and/or associated with the pump drive unit 118. In some embodiments, a rechargeable battery can be wirelessly charged, for example through inductive charging by an inductive charging pad 180. As depicted in FIG. 5B, in some embodiments, the charging pad 180 can include a cover 182 having a cutout sized to receive pump 102 in order to properly position and retain pump 102 on the charging pad 180 during recharging. In some embodiments, as shown in FIGS. 5A, 5B, 5D, the charging pad 180 may receive power by being connected to a wall outlet. In other embodiments, the charging pad 180 may additionally or alternatively include a wired and/or wireless power connection to, for example, a computer (e.g., via USB or IEEE 1394), a 12 volt automobile outlet, a battery pack (e.g., via USB or IEEE 1394), optical means, and a solar panel, among others.

To charge the pump 102, the pump 102 may first be disconnected from the tubing of the infusion set (as depicted in FIG. 5C). The pump can then be placed onto the charging pad 180 (as depicted in FIG. 5D), where its battery will automatically be inductively (re)charged when the pad 180 is connected to a power source. In another embodiment, the pump 102 can remain connected to the infusion set and the user while the battery is recharging. In some embodiments, a pump that can be inductively or otherwise wirelessly charged does not include an external connection port, such as a USB or IEEE 1394 port, into which a power cord can be inserted for power transfer. Such an embodiment provides the advantages of being more robust for waterproofing because of the lack of exposed electrical contacts and obviating electrical isolation requirements imposed upon such connections.

Inductive charging of pump 102 can be carried out according to known standards, such as, for example, the Qi open interface standard. In an example of such a system, both the pump 102 and the charging pad 180 include an inductive coil. A transmitting coil in the charging pad 180 connected to the power source generates an oscillating magnetic field that induces an alternating current in a receiving coil in the pump 102 to transfer power to pump 102. In one embodiment, charging pad 180 continuously (e.g., twice a second) sends an analog signal to detect the presence of a device such as pump 102. When the pad detects the presence of, e.g., a pump (via a magnetic load), it sends a digital communication signal to the pump 102. The pump receives the signal and sends a return signal to the pad 180, which causes the pad 180 to transmit charging power to the pump.

Referring to FIG. 6, a method of enhancing or altering the operation and/or functionality of a single button 172 in the presence of an external electromagnetic signal is depicted in accordance with an embodiment of the disclosure. In other embodiments, the method can alter the function of a plurality of buttons. In one embodiment, at step 201, activation of button 172 can be configured to enable and/or initiate a first function or operation (i.e., function A). The first function can be at least one of, for example, initiating a medicament bolus or delivery of medicament, communicatively coupling the pump to a remote display and/or user interface, communicatively coupling the pump to a remote glucose monitor, initiating a status check, etc. For example, in one embodiment, a single press of button 172 initiates medicament delivery, while a predefined sequential pattern of presses of button 172 over a determined length of time communicatively couples the pump 102 to a remote control device 170 or dedicated remote controller 171. In one embodiment, light source 174, such as an LED, can illuminate to indicate that button 172 has been activated and/or function A has been initiated.

At step 202, a recognized electromagnetic signal is received by pump 102 from another device. For example, the received electromagnetic signal can be a wireless charging signal such as an inductive charging signal. In one embodiment, the inductive charging methodology can require that the pump 102 detect the presence of a charging pad 180 when the charging pad 180 and the pump 102 are in close enough proximity for energy transfer via electromagnetic induction to occur. This communication between the charging pad 180 and the pump 102, sometimes referred to as a "handshake," can aid in ensuring that the charging pad 180 only transmits an inductive charging signal when the pump 102 is present and its battery is ready to receive a charge, and cease transmission once the rechargeable battery has been fully charged, thereby avoiding energy waste and battery overcharging. It is noted that the wireless or inductive "charging signal" as used herein with regard to embodiments of the invention can in various embodiments refer to either the presence detecting signal sent out by the pad to detect the pump, the electromagnetic field or other signal transmitted by the pad to charge the pump, an additional signal transmitted continuously or periodically transmitted by the pad when, for example, the pad is idle or a charge is complete, or some combination thereof.

The received electromagnetic signal can be recognized as an input to software on the pump 102 operated by the pump processor to enable additional features of the pump, either on its own, or in combination with activation of button 172. Thus, at step 203, activation of button 172 can be configured to enable and/or initiate a second function or operation (i.e., function B) different from the first function or operation when the inductive charging signal is present. In one embodiment, the second function can be at least one of, for example, suspending delivery of medicament, initiating a low-power or shelf mode for the pump, resetting the pump processor, communicatively coupling the pump to a remote display and/or user interface, communicatively coupling the pump to a remote glucose monitor, initiating a test routine, initiating a software update protocol, etc. For example, in one embodiment, a single press of button 172 in the presence of inductive charging signal suspends delivery of medicament, while a predefined sequential pattern of presses of button 172 over a determined length of time communicatively resets the pump 102. In one embodiment, light source 174 can illuminate to indicate that button 172 has been activated and/or function B has been initiated.

Although primarily described herein with respect to first and second functions, it should be understood that a plurality of different functions can be addressed by embodiments of the invention. For example, a single press of button 172 may cause the device to execute first and second functions depending on whether or not an electromagnetic signal is present as described herein, whereas a different type of activation of button 172, such, as for example, holding the button down for a predetermined period of time or pressing button 172 a number times within a certain period (e.g., two or three button presses in rapid succession or otherwise recognizable pattern/frequency) can initiate third and fourth or more functions in the absence and presence of such a signal, respectively.

In addition, although primarily described herein with regard to inductive charging, embodiments of the invention can utilize other types of wireless charging. For example, pumps as described herein could alternatively or additionally be charged with resonant wireless charging and RF-based wireless charging and utilize signals related thereto to alter functionality of the pump as described herein.

In another embodiment, the received electromagnetic signal can be a Bluetooth beacon, such as that emitted from the remote control device 170 or dedicated remote controller 171. Such an emitted beacon can have a unique address or name that is recognizable to the pump software when placed within a receivable range of pump 102.

In another embodiment, pump 102 is equipped with one or more accelerometers configured to detect or sense acceleration and/or pump orientation, the input of which can enhance or alter the functionality of button 172, in place of or in addition to an electromagnetic signal. For example, in one embodiment, at step 202, a user can shake the pump 102, either continuously, or for a specified number of times. Alternatively, the one or more accelerometers can detect the pump orientation based on the current orientation or a sequence of orientation shifts. For example, the pump can be held in a vertical orientation until a timeout is achieved, wherein the pump can beep or vibrate to indicate that the time requirement has been met. The pump can then be rotated between about 90 and about 180 degrees to a secondary position and held in that position until a second timeout is achieved. This sequence of orientation shifts can be used to enable pump features and can be useful in production or during patient use for tasks such as cartridge change or priming, to ensure that the pump 102 is in the optimal orientation. The sensed accelerations can be recognized as inputs to software on the pump 102 to enable additional features of the pump, either on its own, or in combination with activation of button 172.

Accordingly, through the receipt of a recognized electromagnetic signal and/or input from internal accelerometers, the functionality of button 172 can be increased, while still maintaining an overall usability of pump 102 that is both intuitive and safe for a user.

Embodiments of the present disclosure enable enhanced or altered operation and/or functionality of an infusion pump, such as a user-wearable infusion pump, in the presence of a recognized electromagnetic signal or following a predefined sequence of accelerometer detected orientation shifts. For example, activation of at least one button on the pump normally enables and/or initiates a first function or operation, such as enabling and/or initiating delivery of medicament, but in the presence of a recognized electromagnetic signal or following a predefined sequence of accelerometer detected orientation shifts, the at least one button can enable and/or initiate a second function or operation different from the first function, such as pairing the pump to a remote device.

Although the pump system described herein is described as a user-wearable pump system that has no display or user interface and is primarily controlled by a remote device, it should be understood that aspects of the present disclosure can be incorporated into other types of infusion pumps. For example, full-featured user-wearable infusion pumps having display and input capabilities, such as a touchscreen display on the pump housing, one example of which is disclosed in U.S. Pat. No. 8,287,495, which is hereby incorporated by reference herein, can incorporate aspects of the present disclosure.

Also incorporated herein by reference in their entirety are commonly owned U.S. Pat. Nos. 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; and 9,750,871 commonly owned U.S. Patent Publication Nos. 2009/0287180; 2012/0123230; 2013/0053816; 2014/0276419; 2014/0276420; 2014/0276423; 2014/0276531; 2014/0276556 2014/0276569; 2014/0276570; 2014/0378898; 2015/0073337; 2015/0182693; 2016/0082188; 2016/0339172; 2017/0049957; 2017/0142658; 2017/0182248; and 2017/0250971 and commonly owned U.S. patent application Ser. Nos. 14/707,851; 15/564,895; and 15/705,983 and commonly owned U.S. Provisional Application Ser. Nos. 61/911,576; 61/920,902; 61/920,914; 61/920,940; 62/139,275; 62/352,164; 62/445,041; and 62/545,228.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A user-wearable infusion pump, comprising:
a reservoir configured to contain a medicament;
a drive mechanism configured to facilitate delivery of the medicament to a user;
a rechargeable battery configured to be charged wirelessly;
an input button; and
a processor functionally linked to the input button and configured to receive input for control of functions of the user-wearable infusion pump in response to input received via the input button, wherein the processor is configured to:
detect a presence of a wireless changing signal:
receive a first input via the input button to cause the user-wearable infusion pump to execute a first function in response to the first input received via the first input button in an absence of the wireless charging signal, the first function being initiating a medicament delivery operation with the user-wearable infusion pump; and
receive a second input via the input button, the second input being the same as the first input, in the presence of the wireless charging signal to cause the user-wearable infusion pump to execute a second function different from the first function when the second input the same as the first input is received in the presence of the wireless charging signal, wherein the second function comprises activating a pairing feature of the user-wearable infusion pump for pairing the user-wearable infusion pump with a remote control.

2. The user-wearable infusion pump of claim 1, wherein the pump includes only a single input button.

3. The user-wearable infusion pump of claim 1, wherein the pump does not include a display screen.

4. The user-wearable infusion pump of claim 3, wherein the processor is further configured to wirelessly communicate pump information to a separate device for display on the separate device.

5. The user-wearable infusion pump of claim 1, further comprising an indicator light.

6. The user-wearable infusion pump of claim 5, wherein the indicator light is functionally linked to the input button such that the indicator light illuminates to indicate that input has been received via the input button.

7. The user-wearable infusion pump of claim 5, wherein the indicator light is functionally linked to the input button such that the indicator light illuminates to indicate when the first function is being executed and when the second function is being executed.

8. The user-wearable infusion pump of claim 7, wherein the indicator light is illuminated differently to indicate when the first function is being executed and when the second function is being executed.

9. The user-wearable infusion pump of claim 1, wherein the wireless charging signal is an inductive charging signal.

10. A user-wearable infusion pump, comprising:
a reservoir configured to contain a medicament;
a drive mechanism configured to facilitate delivery of the medicament to a user;
an input button; and
a processor functionally linked to the input button and configured to receive input for control of functions of the user-wearable infusion pump in response to input received via the input button, wherein the processor is configured to:
- detect a presence of a type of externally originating electromagnetic signal;
- receive a first input via the input button to cause the user-wearable infusion pump to execute a first function directly in response to the first input received via the first input button in an absence of the type of externally originating electromagnetic signal, the first function being initiating a medicament delivery operation with the user-wearable infusion pump; and
- receive a second input via the input button, the second input being the same as the first input when in the presence of the type of externally originating electromagnetic signal,
- to cause the user-wearable infusion pump to execute a second function different from the first function when the second input the same as the first input is received because of the presence of the type of externally originating electromagnetic signal, the second function being activating a pairing feature of the user-wearable infusion pump for pairing the user-wearable infusion pump with a remote control.

11. The user-wearable infusion pump of claim 10, wherein the type of externally originating electromagnetic signal is a wireless charging signal transmitted by a wireless charger.

12. The user-wearable infusion pump of claim 11, wherein the wireless charging signal is an inductive charging signal and the wireless charger is an inductive charger.

13. The user-wearable infusion pump of claim 10, wherein the type of externally originating electromagnetic signal is a BLUETOOTH beacon transmitted by the remote control.

14. The user-wearable infusion pump of claim 13, wherein the BLUETOOTH beacon includes a unique identifier and wherein the processor is further configured to match the unique identifier with a known remote control.

15. The user-wearable infusion pump of claim 13, wherein the remote control is selected from the set consisting of a dedicated remote control for the user-wearable pump and a mobile communication device executing a software application configured to communicate with the user-wearable pump.

16. The user-wearable infusion pump of claim 10, wherein the pump includes only a single input button.

17. The user-wearable infusion pump of claim 10, wherein the pump does not include a display screen.

18. The user-wearable infusion pump of claim 17, wherein the processor is further configured to wirelessly communicate pump information to a separate device for display on the separate device.

19. The user-wearable infusion pump of claim 10, further comprising an indicator light.

20. The user-wearable infusion pump of claim 19, wherein the indicator light is functionally linked to the input button such that the indicator light illuminates to indicate that input has been received via the input button.

21. The user-wearable infusion pump of claim 19, wherein the indicator light is functionally linked to the input button such that the indicator light illuminates to indicate when the first function is being executed and when the second function is being executed.

22. The user-wearable infusion pump of claim 21, wherein the indicator light is illuminated differently to indicate when the first function is being executed and when the second function is being executed.

* * * * *